United States Patent [19]

Van Venrooij et al.

[11] Patent Number: 5,616,685
[45] Date of Patent: Apr. 1, 1997

[54] SNRNP-A ANTIGEN AND FRAGMENTS THEREOF

[75] Inventors: Walter J. Van Venrooij; Peter T. G. Sillekens; Winand J. A. Habets, all of Nijmegen, Netherlands

[73] Assignee: Akzo Nobel N.V., Arnhem, Netherlands

[21] Appl. No.: 319,503

[22] Filed: Oct. 6, 1994

Related U.S. Application Data

[63] Continuation of Ser. No. 908,507, Jun. 30, 1992, abandoned, which is a continuation of Ser. No. 823,051, Jan. 16, 1992, abandoned, which is a continuation of Ser. No. 569,266, Aug. 17, 1990, abandoned, which is a continuation of Ser. No. 260,713, Oct. 21, 1988, abandoned.

[30] Foreign Application Priority Data

Oct. 21, 1987 [NL] Netherlands ............................ 8702510

[51] Int. Cl.⁶ ............................ C07K 7/52; C07K 9/00; A61K 39/00
[52] U.S. Cl. .......................... 530/324; 530/327; 530/328; 424/185.1; 435/69.3
[58] Field of Search ..................................... 530/350, 358, 530/327, 328, 324; 514/7, 12, 14, 16; 435/69.3; 424/185.1

[56] References Cited

U.S. PATENT DOCUMENTS

| | | | |
|---|---|---|---|
| 4,289,690 | 9/1981 | Pestka et al. | 530/351 |
| 4,394,443 | 7/1983 | Weissman et al. | 435/6 |

OTHER PUBLICATIONS

W.J. Habets et al., "Further characterization and subcellular localization of SM and U1 ribonucleoprotein antigens," *Eur. J. Immunol.* 15:992–997 (1985).
Silleken et al. 1987. The EMBO J. 6(12):3841–3848.
Young et al. 1983. Proc. Natl. Acad. Sci. 80:1194–1198.
Ullrich et al. 1984. The EMBO J. 3(2):361–364.
Torczynski et al. 1984. Proc. Natl. Acad. Sci. 81:6451–6455.
Matsudairo, p. 1987. J. Biol. Chem. 262(21):10035–10038.
Hinterberger et al. 1983. J. Biol. Chem. 258(4):2604–2613.
Habet et al. 1985. *The EMBO J.* 4:1545–1550.
Silleken et al. 1987. *The EMBO J.* 6(12):3841–3848, (abstract only from Biosci No. 85047960).
Patton et al. 1989. Mol Cell Biol. 9(8):3360–3348, (abstract only, Medline Accession No. 90014790).
Hardin et al. 1985. Clin. Rheum. Dis. 11(3):485–505, (Abstract Only, Medline Accession No. 86080551).
Sofer et al. 1983, Bio Technique Nov/Dec pp. 198–203.
R. Reuter et al., "Immunuzation of Mice with Purified U1 Small Nuclear Ribonucleoprotein (RNP) Induces a Pattern of Antibody Specificities Characteristic of the Anti–Sm and Anti–RNP Autoimmune Response of Patients with Lupis Erythematosus, as Measured by Monoclonal Antibodies", Proc. Natl. Acad. Sci, vol. 83, pp. 8689–8693, Nov. 1986, USA.
I. Pettersson et al., "The Structure of Mammalian Small Nuclear Ribonucleoproteins", The Journal of Biological Chemistry, vol. 259, No. 9, pp. 5907–5914, May 10, 1984, USA.
P. Bringmann et al., "Purification of the Individual snRNPs U1, U2, U5 and U4/U6 from HeLa Cells and Characterization of their Protein Constituents", The Embo Journal, vol. 5, No. 13, pp. 3509–3516, 1986, Great Britain.
P. Bringmann et al., "Purification of snRNPs U1, U2, U4, U5 and U6 with 2,2,7–trimethylguanosine–specific antibody and definition of their constituent proteins reacting with anti–Sm and anti–(U1) RNP antisera", The EMBO Journal, vol. 2, No. 7, pp. 1129–1135, 1983, Great Britain.
Laemmli, U.K., Nature, 227:680–685, 1970.

*Primary Examiner*—Robert A. Wax
*Assistant Examiner*—William W. Moore
*Attorney, Agent, or Firm*—William M. Blackstone; Gregory R. Muir

[57] ABSTRACT

The present invention relates to a protein antigen which is reactive towards an auto-antibody which is associated with an auto-immune disease, and the use of this protein in diagnostic tests relating to auto-immune diseases.

5 Claims, 3 Drawing Sheets

```
Pro Pro Gly Leu Ala Pro Gly Gln Ile Pro Pro Gly Ala Met Pro Pro Gln Gln
Leu Met Pro Gly Gln Met Pro Pro Ala Gln Pro Leu Ser Glu Asn Pro Pro Asn
```

| | | | | | | | | | | | |
|---|---|---|---|---|---|---|---|---|---|---|---|
| 1 | Met Ala Val Pro Glu Thr Arg Pro Asn His Thr Ile Tyr Ile Asn Asn Leu Asn Glu Lys Ile Lys Lys Asp Glu Leu Lys Lys Ser Leu | | | | | | | | | | 30 |
| 31 | Tyr Ala Ile Phe Ser Gln Phe Gly Gln Ile Leu Asp Ile Leu Val Ser Arg Leu Lys Met Arg Gly Gln Ala Phe Val Ile Phe Lys | | | | | | | | | | 60 |
| 61 | Glu Val Ser Ser Ala Thr Asn Ala Leu Arg Ser Met Gln Gly Phe Pro Phe Tyr Asp Lys Pro Met Arg Ile Gln Tyr Ala Lys Thr Asp | | | | | | | | | | 90 |
| 91 | Ser Asp Ile Ile Ala Lys Met Lys Gly Thr Phe Val Glu Arg Asp Arg Lys Arg Glu Lys Arg Lys Pro Lys Ser Gln Glu Thr Pro Ala | | | | | | | | | | 120 |
| 121 | Thr Lys Lys Ala Val Gln Gly Gly Gly Ala Thr Pro Val Val Gly Ala Val Gln Gly Pro Val Pro Gly Met Pro Pro Met Thr Gln Ala | | | | | | | | | | 150 |
| 151 | Pro Arg Ile Met His His Met Pro Gly Gln Pro Pro Tyr Met Pro Pro Pro Gly Met Ile Pro Pro Pro Gly Leu Ala Pro Gly Gln Ile | | | | | | | | | | 180 |
| 181 | Pro Pro Gly Ala Met Pro Pro Gln Gln Leu Met Pro Gly Gln Met Pro Pro Ala Gln Pro Leu Ser Glu Asn Pro Pro Asn His Ile Leu | | | | | | | | | | 210 |
| 211 | Phe Leu Thr Asn Leu Pro Glu Glu Thr Asn Glu Leu Met Leu Ser Met Leu Phe Asn Gln Phe Pro Gly Phe Lys Glu Val Arg Leu Val | | | | | | | | | | 240 |
| 241 | Pro Gly Arg His Asp Ile Ala Phe Val Glu Phe Asp Asn Glu Val Gln Ala Gly Ala Ala Arg Asp Ala Leu Gln Gly Phe Lys Ile Thr | | | | | | | | | | 270 |
| 271 | Gln Asn Asn Ala Met Lys Ile Ser Phe Ala Lys Lys | | | | | | | | | | |

FIG. 1

Pro Pro Gly Leu Ala Pro Gly Gln Ile Pro Pro Gly Ala Met Pro Pro Gln Gln
Leu Met Pro Gly Gln Met Pro Pro Ala Gln Pro Leu Ser Glu Asn Pro Pro Asn

FIG. 2

Pro Pro Gly Leu Ala Pro Gly Gln Ile Pro Pro Gly Ala Met

FIG. 2a

Phe Leu Thr Asn Leu Pro Glu Glu Thr Asn Glu Leu Met Leu Ser Met Leu Phe Asn Gln Phe Pro Gly Phe Lys Glu Val Arg Leu Val
Pro Gly Arg His Asp Ile Ala Phe Val Glu Phe Asp Asn Glu Val Gln Ala Gly Ala Ala Arg Asp Ala Leu Gln Gly Phe Lys Ile Thr
Gln Asn Asn Ala Met Lys Ile Ser Phe Ala Lys Lys    Asn His Ile Leu

FIG. 3

Pro Gly Arg His Asp Ile Ala Phe Val Glu Phe Asp Asn Glu Val Gln Ala Gly Ala Ala Arg Asp Ala Leu Gln    Pro Gly Phe Lys Glu Val Arg Leu Val

FIG. 3a

Glu Arg Asp Arg Lys Arg Gly Lys Arg Lys

FIG. 4

```
                140             160             180             200             300
atg gca gtt ccc gag acc cgc cct aac cac act att tat atc aac aac ctc aat gag aag aag atc aag aag gat gag cta aaa aag tcc ctg
    220             240             260             280             300
tac gcc atc ttc tcc cag ttt ggc cag atc ctg gat atc ctg gta tca cgg agc ctg aag atg agg ggc cag gcc ttt gtc atc ttc aag
                320             340             360             380             480
gag gtc agc agc gcc acc aac gcc acc ctg cgc tcc atg cag ggt ttc cct ttc tat gac aaa cct atg cgt atc cag tat gcc aag acc gac
    400             420             440             460             480
tca gat atc att gcc aag atg acc ttc gtg gag gac cgc aag cgg gag aag ccc aag agc cag gag acc ccg gcc
                500             520             540             560             660
acc aag aag gct gtg caa ggc ggg gga gcc acc ccc gtg gtg ggg cct gtc ccg atg ccg act cag gcg
    580             600             620             640             660
ccc cgc att atg cac cac atg ccg ggc cag ccg ccc tac atg ccg cct ggt atg atc ccc ccg gcc cct ggc cag atc
                680             700             720             740             840
cca cca ggg gcc atg ccc ccg cag cag ctt atg cca gga cag atg ccc cct cag cct ctt tct gag aat cca ccg aat cac atc ttg
    760             780             800             820             840
ttc ctc acc aac ctg cca gag gag acc aac gag ctc atg ctg tcc atg ctt ttc aat cag ttc cct ggc ttc aag gag gtc cgt ctg gta
                860             880             900             920
ccc ggg cgg cat gac atc gcc ttc gtg gag aat ttt gac ggg gca gct cgc gat gcc ctg cag ggc ttt ctg gta
    940             960
cag aac aac gcc atg aag atc tcc ttt gcc aag aag tag
```

FIG. 5

SNRNP-A ANTIGEN AND FRAGMENTS THEREOF

This is a continuation of U.S. Ser. No. 07/908,507, filed Jun. 30, 1992, now abandoned, which is a file wrapper continuation of U.S. Ser. No 07/823,051, filed Jan. 16, 1992, now abandoned, which is a file wrapper continuation of U.S. Ser. No. 07/569,266, filed Aug. 17, 1990, now abandoned, which is a file wrapper continuation of U.S. Ser. No. 07/260,713, filed Oct. 21, 1988, now abandoned.

The invention relates to a protein antigen which is reactive towards an auto-antibody which is associated with an auto-immune disease, and the use of this protein in diagnostic tests relating to auto-immune diseases.

BACKGROUND OF THE INVENTION

In healthy humans and animals, after the intrusion of a foreign substance (the antigen) the body will attempt to attack this antigen by generating specific antibodies which are directed against this antigen. Most individuals are in general tolerant to substances which occur in their own body. Some individuals on the other hand generate antibodies against endogenous substances, tissues, or components. Such antibodies (auto-antibodies) cause great damage to the organs which contain these endogenous substances. The development of the associated auto-immune disease is in general very slow (a matter of years) and this hampers timely clinical diagnosis and treatment to a high degree. Diagnosis can generally only be made after appreciable damage has already been caused to the body. Earlier research has shown that many of these auto-antibodies are syndrome-specific, i.e. the disease seems to be characterized by the occurrence of specific auto-antibodies.

Furthermore, it appears from recent research that these specific auto-antibodies can often be detected in the serum of a patient long before the clinical diagnosis can be made with certainty. The auto-antibodies therefore predict, as it were, which disease is developing.

The timely detection of these auto-antibodies in the patient's serum is the more important because the patient's treatment can then be initiated earlier, thereby delaying, or even preventing, the often serious damage during the later phase of the disease.

Patients with an auto-immune disease possess auto-antibodies directed against one or more protein antigens, such as small protein molecules which occur in the cell nucleus and which are complexed with ribonucleic acid, such as the so-called snRNPs (small nuclear ribonucleo-proteins).

SUMMARY OF THE INVENTION

A snRNP protein and fragments thereof having a well defined amino acid sequence have now been found, which render it possible to diagnose immune diseases, especially systemic lupus erythematosus (SLE) and mixed connective tissue disease (MCTD), at an early stage.

The invention therefore relates to a protein with the structure as shown in FIG. 1, which protein is substantially free from other natural material, and to fragments thereof which are immunochemically reactive, and to peptides which contain such fragments.

The invention furthermore relates to preparative methods for such a protein, fragment or peptide, to diagnostic methods for the detection of auto-immune antibodies with the aid of such a protein, fragment, or peptide and to test kits for carrying out such diagnostic methods, and to pharmaceutical compositions for combating auto-immune diseases, especially SLE and MCTD, which compositions contain such a protein, fragment or peptide.

The invention furthermore relates to DNA which codes for the protein, the fragments and the peptides according to the invention, to a vector which contains the DNA, and to a host which contains such a vector.

BRIEF DESCRIPTION OF THE DRAWINGS

FIG. 1 illustrates the amino acid sequence of the $U_1$-snRNP-A protein.

FIG. 2 shows the amino acid sequence of a peptide that reacts with antibodies against $U_1$-snRNP-A.

FIG. 2a shows the amino acid sequence of a fragment of the peptide of FIG. 2 that is immunochemically reactive.

FIG. 3 shows the amino acid sequence of a peptide that reacts with antibodies against $U_2$-snRNP-B.

FIG. 3a shows a fragment of the peptide of FIG. 3 that is immunochemically reactive.

FIG. 4 shows the amino acid sequence of a peptide that reacts with antibodies against the Sm protein.

FIG. 5 illustrates the nucleotide sequence coding for the A-protein.

DESCRIPTION OF THE PREFERRED EMBODIMENTS

The protein according to the invention is known in the literature as the $U_1$-snRNP-A protein. This protein, however, has been insufficiently purified in the literature. Structure elucidation has been impossible hitherto.

By using a DNA clone which contains the nucleotide sequence coding for human $U_1$-snRNP-A protein, and which clone was obtained using recombinant DNA techniques known per se, it was possible to elucidate, by techniques known per se, the amino acid sequence of the $U_1$-snRNP-A protein, as is shown in FIG. 1.

Some fragments of the protein according to the invention react specifically with auto-antibodies against the $U_1$-snRNP-A protein. Surprisingly, it has now also been found that other fragments of the protein react with auto-antibodies against the $U_2$-snRNP-B" protein and the Sm protein, two other snRNP proteins. The presence of antibodies against the Sm protein form an indication that the patient is developing SLE, whilst the occurrence of antibodies against the $U_1$-snRNP-A and $U_2$-snRNP-B" proteins provides an indication of MCTD.

The fragments of the protein of FIG. 1 which react with antibodies against $U_1$-snRNP-A, $U_2$-snRNP-B" and Sm protein have the aminoacid sequences shown in FIGS. 2, 3, and 4 respectively. The invention also relates to smaller fragments of these amino acid sequences mentioned provided these smaller fragments are still immunochemically reactive, such as the amino acid sequence of FIG. 2a (being a smaller fragment of the peptide of FIG. 2) and the amino acid sequence of FIG. 3a (being a smaller fragment of the peptide of FIG. 3). The invention further relates to peptides which contain such fragments.

The preparation of these immunochemically reactive protein fragments according to the invention follows known routes, such as chemical synthesis or recombinant DNA techniques.

The protein, the fragments and the peptide according to the invention can be used for the detection of the auto-antibodies mentioned using diagnostic methods known per se for the determination of antibodies by means of antigens reactive with them.

Both homogeneous and heterogeneous diagnostic tests are suitable for this purpose. Use can thus be made of sandwich type tests or of an agglutination test in which, if desired, an inhibition or competition reaction is used.

Suitable tests are those in which a solid phase is used, such as the inner wall of a microassay well, a tube or capillary, a membrane, filter, test strip or the surface of a particle to which an antibody or antigen is bound. For the detection, use is thus made of an antigen or antibody which is provided with a label, such as a radio-active isotope, a dyestuff, metal sol such as a gold sol, an enzyme, or another known label. Methods for the preparation of labelled antigens or antibodies are generally known.

Moreover, the protein, fragments thereof, and peptides which contain such fragments, can be used in suitable pharmaceutical dosage forms against auto-immune diseases. For example, purified $U_1$snRNP-A antigen can be injected intravenously into a patient who is producing antibodies against this antigen. One should administer to a human preferably 1–1000 nanomoles of said A-antigen.

Administration of such a preparation via the circulatory system of a patient with an auto-immune disease results in an antigen-antibody complex formation which can decrease further attack on the abovementioned tissues. The diagnostic methods mentioned can be used to determine the precise quantity of auto-antibodies circulating in the blood. The quantity of the preparation to be administered is determined by the result of said test. The invention is illustrated by reference to the following Examples.

EXAMPLE I

Nucleotide sequence and inferred amino acid sequence of the A protein

Starting from the material lodged with the Central Office for Mould Cultures in Baarn, The Netherlands under number CBS 617.87, the nucleotide sequence of the cDNA inserts has been determined using the so-called dideoxy method described by Sanger et al. (PNAS, 74, 5463–5467, 1977). This nucleotide sequence is shown in FIG. 5. The initiation codon ATG is located at nucleotide position 126.

The stop codon TAG is located at nucleotide position 972, followed by a non-coding region of 223 nucleotides. The inferred amino acid sequence of 282 amino acids for the A protein (FIG. 1) gives a molecular weight of 31.2 kd, which is in good agreement with the observed molecular weight of 32 kd for the A protein analyzed using a SDS-polyacrylamide gel.

EXAMPLE II

Mapping of an antigenic determinant of the A protein

The amino acid sequence of the A protein inferred from the nucleotide sequence as given, has an interesting distribution of charged and aromatic amino acids. These can be assigned to two regions, separated by a segment with a very high proline content (amino acid 140 to 206 in FIG. 1). Most of the charged and aromatic amino acids are located on the N-terminal part of the protein. The amino acid sequence of the A protein, according to FIG. 1, can be split into two parts, namely amino acid 1 to 171 and amino acid 172 to 282. The DNA sequences coding for these sequences, are each placed separately in a suitable expression vector with recombinant DNA techniques know per se. The proteins synthesized by this expression vector are then brought into contact with patient serum containing auto-antibodies via an immunoblotting experiment. Patient serum containing anti-Sm-antibodies reacts specifically with the N-terminal part (amino acid 1 to 171) of the A protein. In this N-terminal part there is a cluster of eleven charged amino acids which represent a hydrophilic section of the A protein (amino acid 103 to 112 in FIG. 1). Hydrophilicity analysis using the Hopp and Woods method supports this site determination. This sequence Glu-Arg-Asp-Arg-Lys-Arg-Glu-Lys-Arg-Lys in the A protein thus forms an epitope which is recognized by patient serum which contains anti-Sm antibodies. Moreover, another unexpected aspect relating to the amino acid sequence of the A protein emerges from this immunoblotting experiment. Both patient serum containing anti-B"-antibodies and patient serum containing anti-A-antibodies react in an immunoblotting experiment with the C-terminal part of the A protein (amino acid 172 to 282 in FIG. 1). If the inferred amino acid sequence of the A protein is laid in a line with the known amino acid sequence of B" protein, on the grounds of this overlap it can then be determined by exclusion that the specific epitope responsible for the antigen character with respect to anti-A-antibodies is located in the A protein in the region of amino acid 172 to 207 according to FIG. 1; this sequence represents a strongly hydrophilic area, and hydrophilicity analysis using the Hopp and Woods method supports this epitope mapping. This also establishes that the epitope which cross-reacts with anti-B"-antibody is located in the region of amino acid 207 to 282 in FIG. 1.

EXAMPLE III

Enzyme Immuno Assay (EIA)

An EIA was set up in which was tested 480 sera from patients with connective tissue diseases. Simultaneously, the same serum samples were tested on immunoblots with eukaryotic nuclear proteins as antigen. The intensity of the reaction on these blots was scored on an arbitrary scale ranging from "very weak" to "strong". When sera were thus grouped on basis of increasing titer of antibodies against eukaryotic A or B" proteins, the signals obtained in the EIA appeared to correlate perfectly with the blotting results; for the two antigens tested, an increased blotting signal corresponded with an increased EIA reading. When patients were subsequently grouped on basis of their diagnosis, it appeared that this simple and sensitive EIA allowed to distinguish between patients with definite SLE and patients with MCTD. Especially the presence of antibodies against the A protein appeared to be diagnostic for MCTD, since they do not, or in very low titers, occur in definite SLE patients.

We claim:

1. An isolated fragment of an snRNP-A antigen having the amino acid sequence of amino acids 1–171 in FIG. 1, wherein said fragment has an epitope recognized by anti-Sm antibodies.

2. The epitope recognized by anti-Sm antibodies according to claim 1, wherein said epitope has the amino acid sequence of FIG. 4.

3. An isolated fragment of an snRNP-A antigen having the amino acid sequence of amino acids 172–282 in FIG. 1, wherein said fragment has an epitope which reacts with antibodies against U1-snRNP-A and has an epitope which reacts with antibodies against U2-snRNP-B".

4. The epitope which reacts with antibodies against U1-snRNP-A according to claim 3, which has an amino acid sequence selected from the group consisting of FIG. 2 and FIG. 2A.

5. The epitope which reacts with antibodies against U2-snRNP-B" according to claim 3, which has an amino acid sequence selected from the group consisting of FIG. 3 and FIG. 3A.

* * * * *